(12) United States Patent
Sato et al.

(10) Patent No.: US 7,288,566 B2
(45) Date of Patent: Oct. 30, 2007

(54) N-HYDROXYFORMAMIDINE DERIVATIVES

(75) Inventors: Masakazu Sato, Tokyo (JP); Hiroyuki Kakinuma, Tokyo (JP); Hideaki Amada, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 266 days.

(21) Appl. No.: 10/527,716

(22) PCT Filed: Sep. 11, 2003

(86) PCT No.: PCT/JP03/11603

§ 371 (c)(1),
(2), (4) Date: Mar. 11, 2005

(87) PCT Pub. No.: WO2004/024677

PCT Pub. Date: Mar. 25, 2004

(65) Prior Publication Data

US 2006/0004078 A1    Jan. 5, 2006

(30) Foreign Application Priority Data

Sep. 12, 2002  (JP)  ............... 2002-266765

(51) Int. Cl.
| C07C 249/04 | (2006.01) |
| C07D 207/06 | (2006.01) |
| A61K 31/40 | (2006.01) |
| A61K 31/155 | (2006.01) |

(52) U.S. Cl. ............... 514/428; 514/633; 548/569; 564/229

(58) Field of Classification Search ............ None
See application file for complete search history.

(56) References Cited

U.S. PATENT DOCUMENTS 6,864,254 B1 * 3/2005 Sato et al. ............ 514/238.8

FOREIGN PATENT DOCUMENTS

| EP | 1 226 819 A1 | 7/2002 |
| EP | 1 291 343 A1 | 3/2003 |
| JP | 2001-354656 A | 12/2001 |
| JP | 2001-354658 A | 12/2001 |
| WO | WO 01/32164 A1 * | 5/2001 |
| WO | WO 01/68610 A1 | 9/2001 |

OTHER PUBLICATIONS

McGiff et al., "20-HETE and the kidney: resolution of old problems and new beginnings," Am. J. Physiol. 1999, vol. 27, pp. R607-R623.*
D.R. Harder, et al. "Role of Cytochrome P-450 Enzymes and Metabolites of Arachidonic Acis in the Control of Vascular Tone" *J. Vasc Res* 1995; 32:79-92.
John C. McGiff, et al. :20-HETE and the kidney: resolution of old problems and new beginnings *Am. J. Physiol.* 1999, vol. 27, pp. R607-R623.
Richard J. Roman "P-450 Metabolites of Aarchidonic Acid in the Control of Cardiovascular Function" *Physiol Rev* 82: 131-185, 2002.

* cited by examiner

*Primary Examiner*—Rebecca Anderson
*Assistant Examiner*—Andrew B. Freistein
(74) *Attorney, Agent, or Firm*—Sughrue Mion Pllc.

(57) ABSTRACT

An N-hydroxyformamidine compound of the following formula or a pharmaceutically acceptable salt thereof:

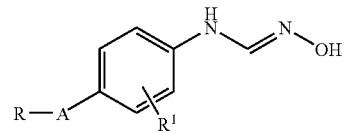

wherein $R^1$, A and R are as defined herein. The compounds inhibit 20-HETE-producing enzymes, 20-HETE being involved in the effects of causing microvascular constriction or dilation in major organs (e.g., kidneys, cerebral blood vessels) or of inducing cell proliferation.

4 Claims, No Drawings

N-HYDROXYFORMAMIDINE DERIVATIVES

This is a National Stage of Application No. PCT/JP03/11603 filed Sep. 11, 2003.

TECHNICAL FIELD

The present invention relates to N-(4-alkyl-substituted phenyl)-N'-hydroxyformamidine derivatives which inhibit enzymes mediating the production of 20-hydroxyeicosatetraenoic acid (20-HETE) biosynthesized from arachidonic acid.

BACKGROUND ART

Prostaglandins produced by cyclooxygenase and leukotrienes produced by lipoxygenase are widely known as physiologically active substances produced from arachidonic acid. However, recent studies have been clarifying a wide variety of in vivo functions of 20-HETE which is produced from arachidonic acid by the action of enzymes belonging to the cytochrome p450 family. Previous reports have indicated that 20-HETE causes microvascular constriction or dilation in major organs (e.g., kidneys, cerebral blood vessels) and induces cell proliferation, thus suggesting that 20-HETE plays an important physiological role in vivo and is deeply involved in the development of various conditions such as kidney diseases, cerebrovascular diseases and cardiovascular diseases (J. Vascular Research, vol. 32, p. 79, 1995, Am. J. Physiol., vol. 277, p. R607, 1999, Physiol. Rev., vol. 82, p. 131, 2002).

Under these circumstances, it has been reported that some N'-hydroxyphenylformamidine derivatives and carboxylic acid derivatives have a strong inhibitory effect against 20-HETE-producing enzymes (International Patent Publication Nos. WO0132164, WO01096309 and WO0168610, Japanese Patent Publication Nos. JP2001354658 and JP2001354656).

DISCLOSURE OF THE INVENTION

The object of the present invention is to provide an agent for inhibiting the production of 20-HETE, which has been shown to be involved in the development of microvascular constriction or dilation in major organs (e.g., kidneys, cerebral blood vessels) or in inducing cell proliferation, etc.

As a result of extensive and intensive efforts made to achieve the object stated above, the inventors of the present invention have found that aromatic compounds having a specific partial structure, i.e., N-(4-alkyl-substituted phenyl)-N'-hydroxyformamidine derivatives unexpectedly have a selective inhibitory effect against 20-HETE-producing enzymes. This finding led to the completion of the present invention. Namely, the present invention provides an N-hydroxyformamidine derivative of the following formula or a pharmaceutically acceptable salt thereof:

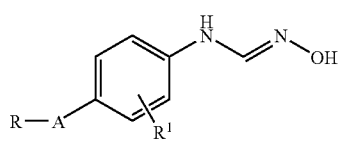

(wherein
$R^1$ represents a hydrogen atom, a $C_{1-4}$ alkyl group, a $C_{1-4}$ alkoxy group or a halogen atom,
A represents a $C_{1-10}$ alkylene group or a group of the following formula:

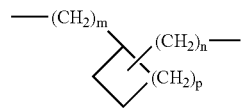

(wherein m, n and p each represent an integer of 0 to 4), and R represents an N,N-di-$C_{1-6}$ alkylamino group, a dioxanyl group, a $C_{1-4}$ alkyl-substituted dioxanyl group, a $C_{1-4}$ alkoxy-$C_{1-4}$ alkoxy group or a group of the following formula:

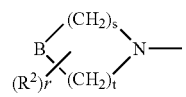

(wherein s and t each represent an integer of 1 to 4, B represents a methylene group, an oxygen atom, a sulfur atom, a nitrogen atom, a $C_{1-4}$ alkyl-substituted nitrogen atom, a phenyl-substituted nitrogen atom or a benzyl-substituted nitrogen atom, $R^2$ represents a hydrogen atom or a $C_{1-4}$ alkyl group, and r represents an integer of 0 to 2)).

In another aspect, the present invention provides an N-hydroxyformamidine derivative of the following formula or a pharmaceutically acceptable salt thereof:

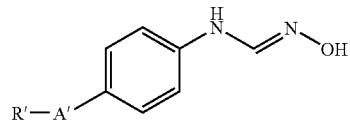

(wherein A' represents a $C_{1-10}$ alkylene group and R' represents an N,N-di-$C_{1-6}$ alkylamino group, a pyrrolidinyl group, a dioxanyl group, a $C_{1-4}$ alkyl-substituted dioxanyl group or a $C_{1-4}$ alkoxy-$C_{1-4}$ alkoxy group).

In another aspect, the present invention provides a pharmaceutical preparation which comprises an N-hydroxyformamidine derivative or a pharmaceutically acceptable salt thereof as an active ingredient.

In another aspect, the present invention provides a N-hydroxyformamidine derivative which is an inhibitor of a 20-HETE-producing enzyme.

In another aspect, the present invention provides a therapeutic agent for kidney diseases, cerebrovascular diseases or cardiovascular diseases, which comprises an N-hydroxyformamidine derivative or a pharmaceutically acceptable salt thereof as an active ingredient.

The terms used herein are defined as follows.

As used herein, the designation "$C_{x-y}$" is intended to mean a group having x to y carbon atoms.

The term "$C_{1-4}$ alkyl group" is intended to mean a linear or branched alkyl group having 1 to 4 carbon atoms. Examples include a methyl group, an ethyl group, a n-propyl group, an isopropyl group and a n-butyl group. The term "$C_{1-4}$ alkoxy group" is intended to mean a linear or branched alkoxy group having 1 to 4 carbon atoms. Examples include a methoxy group, an ethoxy group, a n-propoxy group, an isopropoxy group and a n-butoxy group.

The term "N,N-di-$C_{1-6}$ alkylamino group" is intended to include an N,N-dimethylamino group, an N,N-diethylamino group and the like.

A group of the following formula:

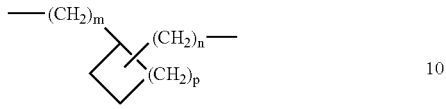

refers to a $C_{3-7}$ cycloalkane modified to have two alkylene groups or binding hands. Preferred are those in which p is 0 to 3, and m and n are each 1 to 3, as exemplified by the groups shown below.

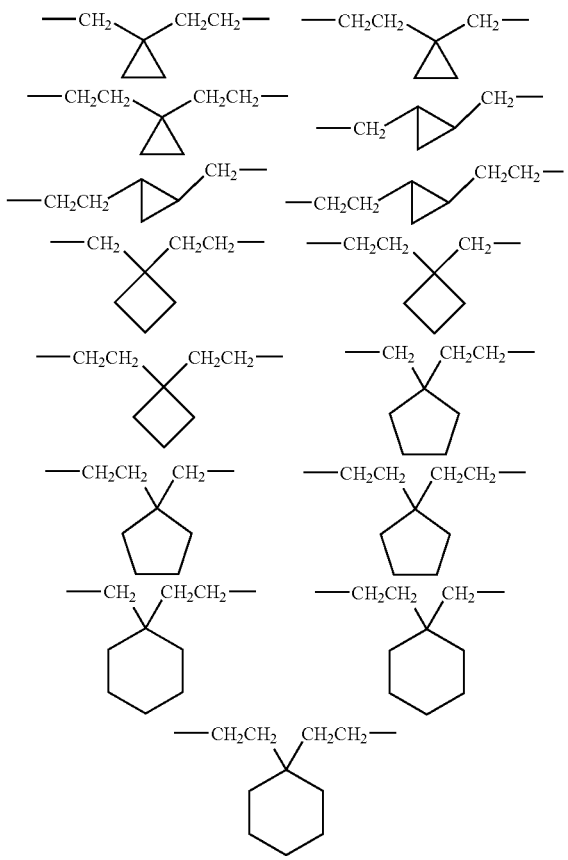

The term "dioxanyl group" is intended to mean a saturated 6-membered ring having two oxygen atoms as heteroatoms (dioxane), preferably a monovalent group derived by removing hydrogen from the 1,3-dioxane ring.

With respect to the term "$C_{1-4}$ alkyl-substituted dioxanyl group," its ring may be substituted with a $C_{1-6}$ alkyl group. Examples include a 5,5-dimethyl-1,3-dioxan-2-yl group.

The term "$C_{1-4}$ alkoxy-$C_{1-4}$ alkoxy group" is intended to mean a structure composed of two $C_{1-4}$ alkoxy groups. Preferred examples include a methoxyethoxy group, an ethoxyethoxy group, a n-butoxyethoxy group and an isobutoxyethoxy group.

The term "$C_{1-10}$ alkylene group" is intended to mean a linear or branched alkylene group having 1 to 10 carbon atoms. Examples include a methylene group, a methylmethylene group, an ethylene group, a propylene group, a heptylene group, a 2,2-dimethylpropylene group, a 3,3-dimethylpropylene group and a hexylene group. Among them, preferred are an ethylene group and a 3,3-dimethylpropylene group.

A group of the following formula:

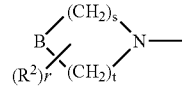

is intended to include a pyrrolidino group, a piperidino group, a morpholino group, a thiomorpholino group, a 4-methylpiperazin-1-yl group and a 3,5-dimethylmorpholino group.

In addition, the term "pharmaceutically acceptable salt" is intended to mean, for example, a salt with an alkali metal, an alkaline earth metal, ammonium or an alkylammonium, or a salt with a mineral acid or an organic acid. Examples include a sodium salt, a potassium salt, a calcium salt, an ammonium salt, an aluminum salt, a triethylammonium salt, an acetate, a propionate, a butyrate, a formate, a trifluoroacetate, a maleate, a tartrate, a citrate, a stearate, a succinate, an ethylsuccinate, a lactobionate, a gluconate, a glucoheptate, a benzoate, a methanesulfonate, an ethanesulfonate, a 2-hydroxyethanesulfonate, a benzenesulfonate, a p-toluenesulfonate, a lauryl sulfate, a malate, an aspartate, a glutamate, an adipate, a salt with cysteine, a salt with N-acetylcysteine, a hydrochloride, a hydrobromide, a phosphate, a sulfate, a hydroiodide, a nicotinate, an oxalate, a picrate, a thiocyanate, an undecanoate, a salt with an acrylate polymer and a salt with a carboxyvinyl polymer.

The compound of the present invention can be synthesized in the following manner, by way of example.

Production Process 1

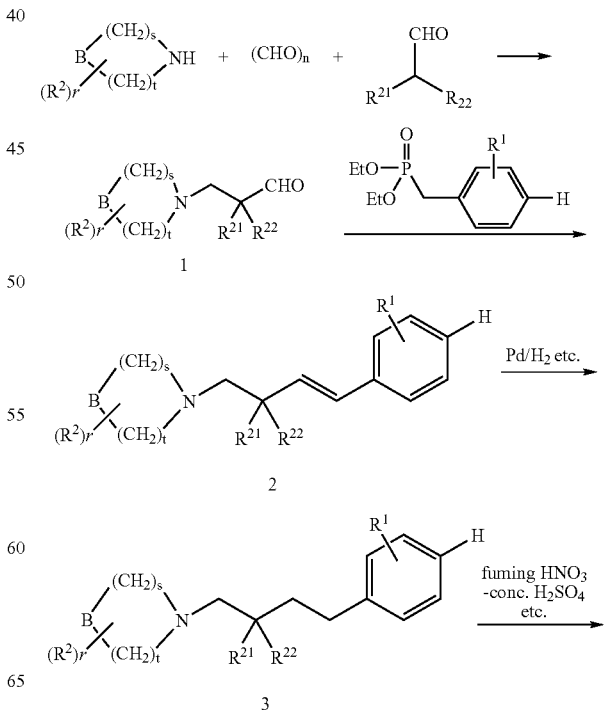

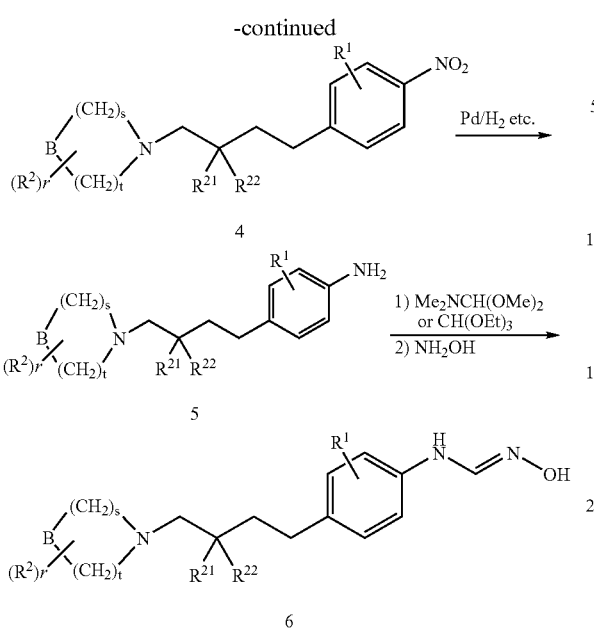

(wherein B, $R^1$, $R^2$, r, s and t are as defined above, $R^{21}$ and $R^{22}$ each represent a $C_{1-4}$ alkyl group or together form a $C_{3-7}$ cycloalkane ring).

Aldehyde 1 synthesized via Mannich reaction and the Horner-Emmons reagent (e.g., diethyl benzylphosphonate) may be reacted at −78° C. to room temperature for 1 to 24 hours in an appropriate solvent (e.g., tetrahydrofuran, ether, toluene, N,N-dimethylformamide) and in the presence of an appropriate base (e.g., n-butyllithium, triethylamine, N,N-diisopropylethylamine, sodium hydride, sodium methoxide, potassium tert-butoxide) to prepare Compound 2. Compound 2 may then be reacted under a hydrogen atmosphere in the presence of a catalyst (e.g., palladium-activated charcoal, palladium hydroxide) and in an appropriate solvent (e.g., methanol, ethanol, propanol, tetrahydrofuran, dioxane, toluene, methylene chloride, chloroform, acetonitrile, ethyl acetate) to prepare Compound 3. Compound 3 may then be nitrated under certain conditions, e.g., fuming nitric acid-concentrated sulfuric acid, potassium nitrate-concentrated sulfuric acid, or cerium(IV) diammonium nitrate-concentrated sulfuric acid, to prepare a nitro derivative (4). Compound 4 may then be treated in an appropriate solvent (e.g., methanol, ethanol, propanol, tetrahydrofuran, dioxane, toluene, methylene chloride, chloroform, acetonitrile, ethyl acetate) using a reducing agent (e.g., palladium-activated charcoal/under a hydrogen atmosphere, palladium-activated charcoal/hydrazine hydrate, palladium-activated charcoal/ammonium formate, tin(II) chloride monohydrate, iron/ammonium chloride, Raney Nickel/hydrazine hydrate, preferably palladium-activated charcoal/under a hydrogen atmosphere) to reduce the nitro group, thereby preparing an aniline derivative (5).

Subsequently, Compound 5 may be reacted with N,N-dimethylformamide dimethyl acetal at room temperature to 150° C., preferably 70° C. to 100° C., for 2 to 72 hours in an appropriate solvent (e.g., methanol, ethanol, propanol, tetrahydrofuran, dioxane, toluene, methylene chloride, chloroform, acetonitrile, ethyl acetate). The resulting intermediate may be treated with hydroxylammonium chloride in an appropriate solvent (e.g., methanol, ethanol, propanol, tetrahydrofuran, dioxane, toluene, methylene chloride, chloroform, acetonitrile, ethyl acetate) to prepare Compound 6 according to the present invention. Alternatively, Compound 5 may also be reacted with an orthoformate ester (e.g., trimethyl orthoformate, triethyl orthoformate) in the presence or absence of a catalytic amount of an organic acid (e.g., acetic acid), a mineral acid (e.g., hydrochloric acid), pyridine hydrochloride or the like to give an intermediate. The reaction temperature ranges from room temperature to 150° C., preferably 70° C. to 100° C., while the reaction time ranges from 2 to 72 hours. Either with or without isolation, the intermediate may be treated with hydroxylamine in an appropriate solvent (e.g., methanol, ethanol, propanol, tetrahydrofuran, dioxane, toluene, methylene chloride, chloroform, acetonitrile, ethyl acetate) to prepare Compound 6 according to the present invention.

Alternatively, a compound of the following formula (synthesized as described in J Org Chem vol. 53, p. 3309, 1988):

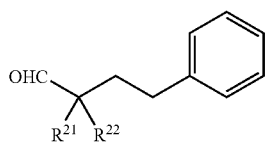

(wherein $R^{21}$ and $R^{22}$ are as defined above) and an amine of the following formula:

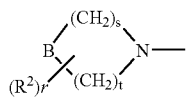

(wherein B, $R^2$, r, s and t are as defined above) may be subjected to reductive alkylation to give Synthetic Intermediate 3. Using this synthetic intermediate, the same procedure may be repeated to prepare Compound 6 according to the present invention.

Production Process 2

A compound of the following formula (synthesized as described in Org Letter vol. 4, p. 1951, 2002):

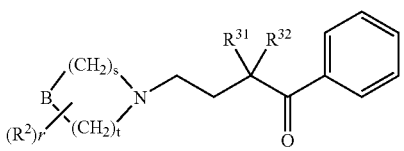

(wherein B, $R^2$, r, s and t are as defined above, and $R^{31}$ and $R^{32}$ each represent a $C_{1-4}$ alkyl group or together form a $C_{3-7}$ cycloalkane ring) may be reduced via Wolff-Kishner reaction or the like, or alternatively, a compound of the following formula (synthesized as described in Tetrahedron, vol. 46, p. 2111, 1990):

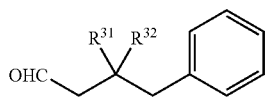

(wherein $R^{31}$ and $R^{32}$ are as defined above) and an amine of the following formula:

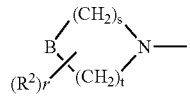

(wherein B, $R^2$, r, s and t are as defined above) may be subjected to reductive alkylation to give a synthetic intermediate of the following formula:

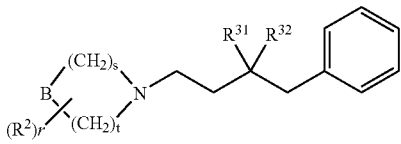

(wherein B, $R^2$, r, s, t, $R^{31}$ and $R^{32}$ are as defined above). Using this synthetic intermediate, the same procedure as shown in Production Process 1 may be repeated to synthesize the compound of the present invention represented by the following formula:

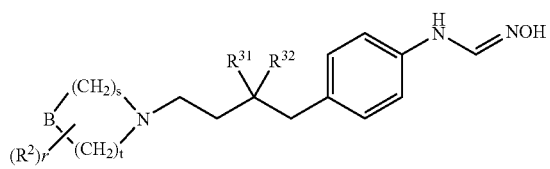

(wherein B, $R^2$, r, s, t, $R^{31}$ and $R^{32}$ are as defined above).

Production Process 3

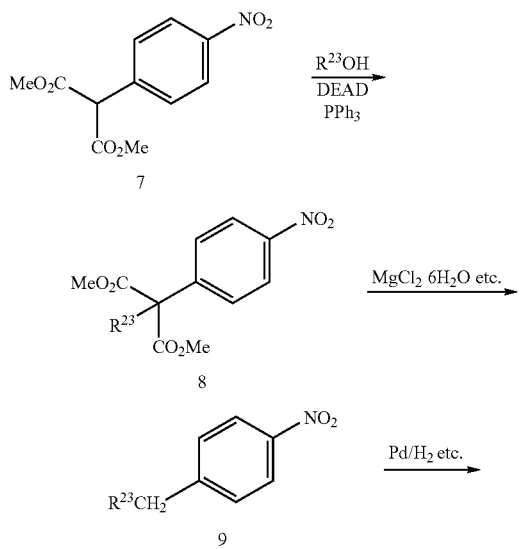

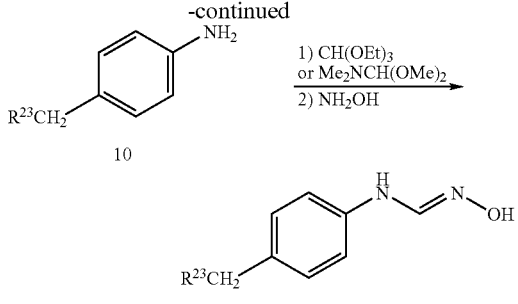

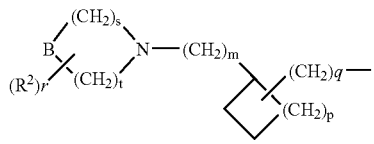

2-(4-Nitrophenyl)malonic acid dimethyl ester (7) may be condensed with an alcohol of the formula $R^{23}OH$ (wherein $R^{23}$ represents a $C_{1-4}$ alkoxy-$C_{1-3}$ alkyl group, an N,N-di-$C_{1-6}$ alkylamino-$C_{1-9}$ alkyl group or a group of the following formula:

(wherein B, $R^2$, r, s, t, m and p are as defined above, and q represents an integer of 0 to 3)) via Mitsunobu reaction to synthesize Compound 8 (Tetrahedron Lett., vol. 42, p. 8395, 2001). Compound 8 may then be treated with NaCl or $MgCl_2.6H_2O$ in an appropriate solvent (e.g., N,N-dimethylacetamide, DMSO, DMSO-$H_2O$) to synthesize Compound 9. The reaction temperature ranges from 100° C. to 150° C., and the reaction time ranges from 5 to 24 hours (Synthesis, vol. 12, p. 1659, 2000). Subsequently, the nitro group may be reduced in the same manner as shown in Production Process 1 to synthesize an aniline derivative (10). At the end of the process, hydroxyformamidine may be constructed in the same manner as shown in Production Process 1 to prepare Compound 11 according to the present invention.

BEST MODE FOR CARRYING OUT THE INVENTION

The present invention will be further described in more detail in the following examples.

EXAMPLE 1

Preparation of N-[4-(4-N,N-dimethylamino-3,3-dimethyl-butyl)phenyl]-N'-hydroxyformamidine (1) To a mixture of dimethylamine hydrochloride (10.8 g, 0.132 mol) and 2-propanol (62 ml), paraformaldehyde (8.7 g) and isobutyl aldehyde (12 ml, 0.132 mol) were added. The reaction mixture was stirred under heating at reflux overnight. After cooling to room temperature, the reaction mixture was concentrated. The residue was diluted with saturated aqueous sodium bicarbonate and extracted with ethyl acetate (100 ml×5). The combined organic layers were dried over anhydrous magnesium sulfate and concentrated under reduced pressure to give 3-dimethylamino-2,2-dimethylpropionaldehyde (8.4 g) as a colorless oil.

(2) A mixture of diethyl benzylphosphonate (7.4 g, 0.0325 mol) and THF (32 ml) was cooled to −78° C., followed by addition of n-BuLi (1.6 M in n-hexane, 19.4 mL, 0.0311 mol) under a nitrogen stream. After 15 minutes, a solution of 3-dimethylamino-2,2-dimethylpropionaldehyde (3.5 g, 0.0271 mol) in THF (20 ml) was added dropwise. After stirring for 30 minutes, the reaction mixture was warmed to room temperature, diluted with water (50 ml), and extracted twice with ethyl acetate. The combined organic layers were washed with saturated aqueous sodium chloride, dried over anhydrous magnesium sulfate, and concentrated under reduced pressure. The residue was purified by NH silica gel column chromatography (hexane:ethyl acetate=96:4) to give (2,2-dimethyl-4-phenyl-3-butenyl)dimethylamine (3.3 g) as a colorless oil.

(3) A methanol solution of (2,2-dimethyl-4-phenyl-3-butenyl)dimethylamine (3.0 g, 0.015 mol) was stirred overnight in the presence of 10% palladium-activated charcoal (0.3 g) under a hydrogen atmosphere. The insoluble materials were removed by filtration through celite and the resulting filtrate was concentrated to give (2,2-dimethyl-4-phenylbutyl)dimethylamine (2.9 g) as a colorless crystal.

(4) To a mixture of (2,2-dimethyl-4-phenylbutyl)dimethylamine (2.9 g, 0.014 mol), concentrated sulfuric acid (15 ml) and chloroform (29 ml), fuming nitric acid (0.58 ml, 0.014 mol) was slowly added dropwise while vigorously stirring the mixture under ice cooling. After 10 minutes, 5M sodium hydroxide (90 ml) was added to adjust the reaction mixture to pH 8.0. The reaction mixture was further diluted with water (500 ml) and extracted twice with ethyl acetate. The combined organic layers were dried over anhydrous magnesium sulfate and concentrated under reduced pressure. The residue was purified by NH silica gel column chromatography (hexane:ethyl acetate=92:8) to give a mixture of [2,2-dimethyl-4-(4-nitrophenyl)butyl]dimethylamine and [2,2-dimethyl-4-(2-nitrophenyl)butyl]dimethylamine (10:1; 0.45 g) as a yellow oil.

(5) A methanol solution of [2,2-dimethyl-4-(4-nitrophenyl)butyl]dimethylamine (400 mg, 1.60 mmol) was stirred in the presence of 10% palladium-activated charcoal (40 mg) under a hydrogen atmosphere for 3 hours. The insoluble materials were removed by filtration through celite and the resulting filtrate was concentrated to give 4-(4-dimethylamino-3,3-dimethylbutyl)aniline (290 mg) as a red oil.

Subsequently, to a solution of 4-(4-dimethylamino-3,3-dimethylbutyl)aniline (200 mg, 0.908 mmol) in methanol (4 ml), N,N-dimethylformamide dimethyl acetal (0.48 ml, 3.6 mmol) was added and then stirred under heating at reflux overnight. After cooling to room temperature, the reaction mixture was mixed with hydroxylammonium chloride (315 mg, 4.54 mmol) and stirred at room temperature for 78 hours. The reaction mixture was concentrated, followed by the addition of 2.5 M sodium hydroxide, and then, extracted three times with ethyl acetate. The combined organic layers were dried over anhydrous magnesium sulfate and concentrated under reduced pressure. The residue was recrystallized from a mixed solvent of hexane and ethyl acetate to give the titled compound (68 mg) as a colorless powder.

$^1$H-NMR (300 MHz, DMSO-$d_6$) δ: 0.87 (s, 6H), 1.39-1.45 (m, 2H), 2.08 (s, 2H), 2.23 (s, 6H), 2.38-2.44 (m, 2H), 6.98-7.05 (m, 4H), 7.38 (d, J=10.7 Hz, 1H), 8.39 (d, J=10.7 Hz, 1H), 9.73 (s, 1H) Melting point: 124.0-126.0° C.

EXAMPLE 2

Preparation of N-[4-(4-N,N-diethylamino-3,3-dimethyl-butyl)phenyl]-N'-hydroxyformamidine The same procedure as used in Example 1 was repeated to synthesize the titled compound.

$^1$H-NMR (300 MHz, DMSO-$d_6$) δ: 0.86 (s, 6H), 0.93 (t, J=7.2 Hz, 6H), 1.42-1.36 (m, 2H), 2.17 (s, 2H), 2.39-2.45 (m, 2H), 2.47-3.31 (m, 4H), 6.98-7.05 (m, 4H), 7.38 (d, J=10.7 Hz, 1H), 8.39 (d, J=10.7 Hz, 1H), 9.75 (s, 1H) Melting point: 95.5-97.5° C. (colorless powder)

EXAMPLE 3

Preparation of N-[4-(4-pyrrolidin-1-yl-3,3-dimethyl-butyl)phenyl]-N'-hydroxyformamidine The same procedure as used in Example 1 was repeated to synthesize the titled compound.

$^1$H-NMR (300 MHz, DMSO-$d_6$) δ: 1.40-1.46 (m, 2H), 1.64-1.68 (m, 4H), 2.29 (s, 2H), 2.53-2.58 (m, 2H), 6.98-7.05 (m, 4H), 7.38 (d, J=10.7 Hz, 1H), 8.39 (d, J=10.7 Hz, 1H), 9.75 (s, 1H) Melting point: 120.0-121.5° C. (colorless powder)

EXAMPLE 4

Preparation of N-[4-(4-N,N-diethylaminobutyl)phenyl]-N'-hydroxyformamidine (1) To a solution of 4-(4-nitrophenyl)butyric acid (1.0 g, 4.78 mmol) and diethylamine (0.699 g, 9.56 mmol) in N,N-dimethylformamide (10 ml), N-ethyl-N'-3-dimethylaminopropylcarbodiimide hydrochloride (1.37 g, 7.17 mmol) and 1-hydroxybenzotriazole monohydrate (0.969 g, 7.17 mmol) were added and stirred at room temperature for 24 hours. After addition of water, the reaction mixture was extracted twice with ethyl acetate. The combined organic layers were washed with saturated aqueous sodium bicarbonate, dried over anhydrous magnesium sulfate, and then concentrated under reduced pressure to give N,N-diethyl-4-(4-nitrophenyl)butylamide (1.4 g) as a light-yellow oil.

To a mixture of N,N-diethyl-4-(4-nitrophenyl)butylamide (1.4 g) and THF (14 ml), 1M BH$_3$.THF (9.6 ml) was added dropwise and stirred overnight at room temperature. After 1M BH$_3$.THF (7.0 ml) was further added dropwise, the reaction mixture was stirred at room temperature for 6 hours, followed by addition of 50% acetic acid (3 ml). The reaction mixture was concentrated, followed by the addition of saturated aqueous sodium bicarbonate, and then, extracted twice with ethyl acetate. The combined organic layers were washed with saturated aqueous sodium chloride, dried over anhydrous magnesium sulfate, and then concentrated under reduced pressure to give diethyl-[4-(4-nitrophenyl)butyl]amine (1.74 g) as a light-yellow oil.

(3) A methanol solution of diethyl-[4-(4-nitrophenyl)butyl]amine (1.74 g) was stirred in the presence of 10% palladium-activated charcoal (0.3 g) under a hydrogen atmosphere for 3 hours. The insoluble materials were removed by filtration through celite and the resulting filtrate was concentrated. The residue was purified by NH silica gel column chromatography (hexane:ethyl acetate=2:1) to give 4-(4-diethylaminobutyl)-aniline (998 mg) as an oil.

(4) To a solution of 4-(4-diethylaminobutyl)-aniline (676 mg, 3.12 mmol) in methanol (4 ml), N,N-dimethylformamide dimethyl acetal (0.83 ml, 6.2 mmol) was added. The reaction mixture was stirred under heating at reflux for 1 hour. After cooling to room temperature, the reaction mixture was mixed with hydroxylammonium chloride (433 mg, 6.24 mmol) and stirred at room temperature for 90 hours. The reaction mixture was concentrated, diluted with saturated aqueous sodium bicarbonate, and extracted twice with ethyl acetate and five times with chloroform. The combined organic layers were dried over anhydrous magnesium sulfate and concentrated under reduced pressure. The residue was purified by NH silica gel column chromatography (hexane:ethyl acetate=5:95). The resulting solid was recrystallized from a mixed solvent of hexane and ethyl acetate to give the titled compound (314 mg) as a colorless powder.

$^1$H-NMR (300 MHz, DMSO-$d_6$) δ: 0.92 (t, J=7.3 Hz, 6H), 1.24-1.60 (m, 4H), 2.26-2.45 (m, 8H), 6.99-7.08 (m, 4H), 7.39 (d, J=11.0 Hz, 1H), 8.42 (d, J=11.0 Hz, 1H), 9.77 (s, 1H) Melting point: 110.0-113.0° C.

EXAMPLE 5

Preparation of N-{4-[3-(2-methoxyethoxy)propyl]phenyl}-N'-hydroxyformamidine (1) To a solution of triphenylphosphine (4.81 g, 18.3 mmol) in tetrahydrofuran (20 ml) cooled to 0° C., diethyl azodicarboxylate (40% in toluene; 7.99 g, 18.3 mmol) and diethylene glycol monomethyl ether (2.21 g, 18.4 mmol) were added sequentially. The reaction mixture was warmed to room temperature and stirred for 30 minutes. After cooling to 0° C. again, a solution of 2-(4-nitrophenyl)malonic acid dimethyl ester (3.10 g, 12.2 mmol) in tetrahydrofuran (50 ml) was added dropwise. The reaction mixture was warmed to room temperature, stirred overnight at room temperature, and then reacted at 60° C. for 5.5 hours. After addition of ethyl acetate, the reaction mixture was washed with saturated aqueous sodium chloride, dried over anhydrous magnesium sulfate, and then concentrated under reduced pressure. The resulting residue was purified by silica gel column chromatography (hexane:ethyl acetate=4:1 to 2:1), followed by NH silica gel column chromatography (hexane:ethyl acetate=4:1) to give 2-[2-(2-methoxyethoxy)ethyl]-2-(4-nitrophenyl)malonic acid dimethyl ester (1.80 g) as a light-yellow oil.

(2) To a solution of 2-[2-(2-methoxyethoxy)ethyl]-2-(4-nitrophenyl)malonic acid dimethyl ester (1.13 g, 3.2 mmol) in N,N-dimethylacetamide (6 ml), magnesium chloride hexahydrate (1.30 g, 6.4 mmol) was added and reacted at 150° C. for 10 hours. The reaction mixture was cooled to room temperature, diluted with ethyl acetate, and washed with saturated aqueous sodium chloride. The organic layer was dried over anhydrous magnesium sulfate and concentrated under reduced pressure. The resulting residue was purified by silica gel column chromatography (hexane:ethyl acetate=4:1 to 2:1) to give 1-[3-(2-methoxyethoxy)propyl]-4-nitrobenzene (0.52 g) as a yellow oil.

(3) A solution of 1-[3-(2-methoxyethoxy)propyl]-4-nitrobenzene (0.49 g, 2.1 mmol) in methanol (10 ml) was stirred in the presence of 5% palladium-activated charcoal (0.20 g) under a hydrogen atmosphere at room temperature for 1 hour. After confirming the disappearance of starting materials by TLC analysis, the insoluble materials were removed by filtration using celite and the filtrate was concentrated under reduced pressure. The resulting residue was purified by silica gel column chromatography (hexane:ethyl acetate=7:3 to 1:1) to give 4-[3-(2-methoxyethoxy)propyl]phenylamine (0.38 g) as a light-yellow oil.

(4) To a solution of 4-[3-(2-methoxyethoxy)propyl]phenylamine (0.20 g, 0.97 mmol) in methanol (5 ml), N,N-dimethylformamide dimethyl acetal (0.24 g, 2.0 mmol) was added and reacted at 100° C. for 4.5 hours. After cooling to room temperature, the reaction mixture was mixed with hydroxylamine monohydrochloride (0.14 g, 1.9 mmol) and stirred overnight at room temperature. After further addition of hydroxylamine monohydrochloride (0.067 g, 0.96 mmol), the reaction mixture was reacted at room temperature for 1.5 hours and at 50° C. for 5.5 hours. The reaction mixture was cooled to room temperature, diluted with saturated aqueous sodium chloride, and extracted with ethyl acetate. The organic layer was dried over anhydrous magnesium sulfate and concentrated under reduced pressure. The resulting residue was purified by NH silica gel column chromatography (hexane:ethyl acetate=1:1 to 1:2) to give the titled compound (0.14 g) as a light-green oil.

$^1$H-NMR (300 MHz, DMSO-$d_6$) δ: 1.66-1.78 (m, 2H), 3.25 (s, 3H), 3.26-3.39 (m, 4H), 3.40-3.51 (m, 4H), 7.00-7.10 (m, 4H), 7.40 (d, J=10.7 Hz, 1H), 8.42 (d, J=10.7 Hz, 1H), 9.76 (s, 1H)

EXAMPLE 6

Preparation of N-{4-[6-(N,N-dimethylamino)hexyl]phenyl}-N'-hydroxyformamidine

Starting with 5-(N,N-dimethylamino)pentanol instead of diethylene glycol monomethyl ether, the same procedure as used in Example 5 was repeated to synthesize the titled compound.

Melting point: 96.0-97.0° C. (colorless powder)

EXAMPLE 7

Preparation of N-{4-[2-(5,5-dimethyl-[1,3]dioxan-2-yl)ethyl]phenyl}-N'-hydroxyformamidine (1) To a solution of ethyl 4-nitrocinnamate (3.18 g, 14.4 mmol) in tetrahydrofuran (30 ml), diisobutylaluminum hydride (1.0 M in toluene; 14.4 ml, 14.4 mmol) was added dropwise at −78° C. and stirred at −78° C. for 1 hour. After further addition of diisobutylaluminum hydride (1.0 M in toluene; 28.7 ml, 28.7 mmol), the reaction mixture was reacted at −78° C. for 30 minutes. Aqueous hydrochloric acid (1M) was gradually added to the reaction mixture, followed by extraction with ethyl acetate. The organic layer was dried over anhydrous magnesium sulfate and concentrated under reduced pressure. The resulting residue was purified by silica gel column chromatography (hexane:ethyl acetate=2:1 to 1:3) to give 3-(4-nitrophenyl)propyl-2-en-1-ol (2.16 g) as a yellow powder.

Melting point: 124.5-126.0° C.

(2) To a solution of 3-(4-nitrophenyl)propyl-2-en-1-ol (0.67 g, 3.8 mmol) in methylene chloride (40 ml), activated manganese dioxide (5.01 g) was added and reacted at room temperature for 2 hours. The insoluble materials were filtered on celite and washed with chloroform. The filtrate was concentrated under reduced pressure and the resulting residue was purified by silica gel column chromatography (hexane:ethyl acetate=6:1 to 3:1) to give 13-(4-nitrophenyl)propenal (0.55 g) as a light-yellow powder.

Melting point: 140.0-141.5° C.

(3) To a solution of 3-(4-nitrophenyl)propenal (0.51 g, 2.9 mmol) in benzene (40 ml), p-toluenesulfonic acid monohydrate (0.059 g, 0.3 mmol) and 2,2-dimethylpropane-1,3-diol (0.36 g, 3.5 mmol) were added and reacted under heating at reflux for 5 hours. The reaction mixture was cooled to room temperature, followed by the addition of saturated aqueous sodium bicarbonate (100 ml), and then, extracted twice with ethyl acetate (100 ml). The combined organic layers were dried over anhydrous magnesium sulfate and concentrated under reduced pressure. The resulting residue was purified by silica gel column chromatography (hexane:ethyl acetate=9:1 to 6:1) to give 5,5-dimethyl-2-[2-(4-nitrophenyl)vinyl]-[1,3]dioxane (0.73 g) as a colorless powder.

Melting point: 86.5-88.5° C.

(4) A solution of 5,5-dimethyl-2-[2-(4-nitrophenyl)vinyl]-[1,3]dioxane (0.64 g, 2.4 mmol) in methanol (20 ml) was stirred in the presence of 5% palladium-activated charcoal (0.26 g) under a hydrogen atmosphere at room temperature for 4 hours. After confirming the disappearance of starting materials by TLC analysis, the insoluble materials were removed by filtration using celite and the filtrate was concentrated under reduced pressure. The resulting residue was purified by silica gel column chromatography (hexane:ethyl acetate=4:1 to 2:1) to give 4-[2-(5,5-dimethyl-[1,3]dioxan-2-yl)ethyl]phenylamine (0.48 g) as a colorless powder.

Melting point: 93.5 to 94.5° C.

(5) To a solution of 4-[2-(5,5-dimethyl-[1,3]dioxan-2-yl)ethyl]phenylamine (0.32 g, 1.4 mmol) in methanol (10 ml), N,N-dimethylformamide dimethyl acetal (0.33 g, 2.8 mmol) was added and reacted at 100° C. for 4 hours. After cooling to room temperature, the reaction mixture was mixed with hydroxylamine monohydrochloride (0.14 g, 1.9 mmol) and stirred overnight at room temperature. After addition of hydroxylammonium chloride (0.19 g, 2.8 mmol), the reaction mixture was reacted at room temperature for 1 hour and at 60° C. for 6.5 hours. The reaction mixture was cooled to room temperature, followed by the addition of saturated aqueous sodium chloride, and then, extracted with ethyl acetate. The organic layer was dried over anhydrous magnesium sulfate and concentrated under reduced pressure. The resulting residue was purified by NH silica gel column chromatography (hexane:ethyl acetate=2:1 to 1:2) to give the titled compound (0.25 g) as a colorless powder.

Melting point: 159.0-160.0° C.

EXAMPLE 8

Preparation of N-{4-[3-(5,5-dimethyl-[1,3]dioxan-2-yl)propyl]phenyl}-N'-hydroxyformamidine Starting with 4-(4-nitrophenyl)butyric acid instead of ethyl 4-nitrocinnamate, the same procedure as used in Example 7 was repeated to synthesize the titled compound.

Melting point: 138.0-140.0° C. (colorless powder)

The structural formulae of the compounds synthesized in Examples 1 to 8 will be shown below.

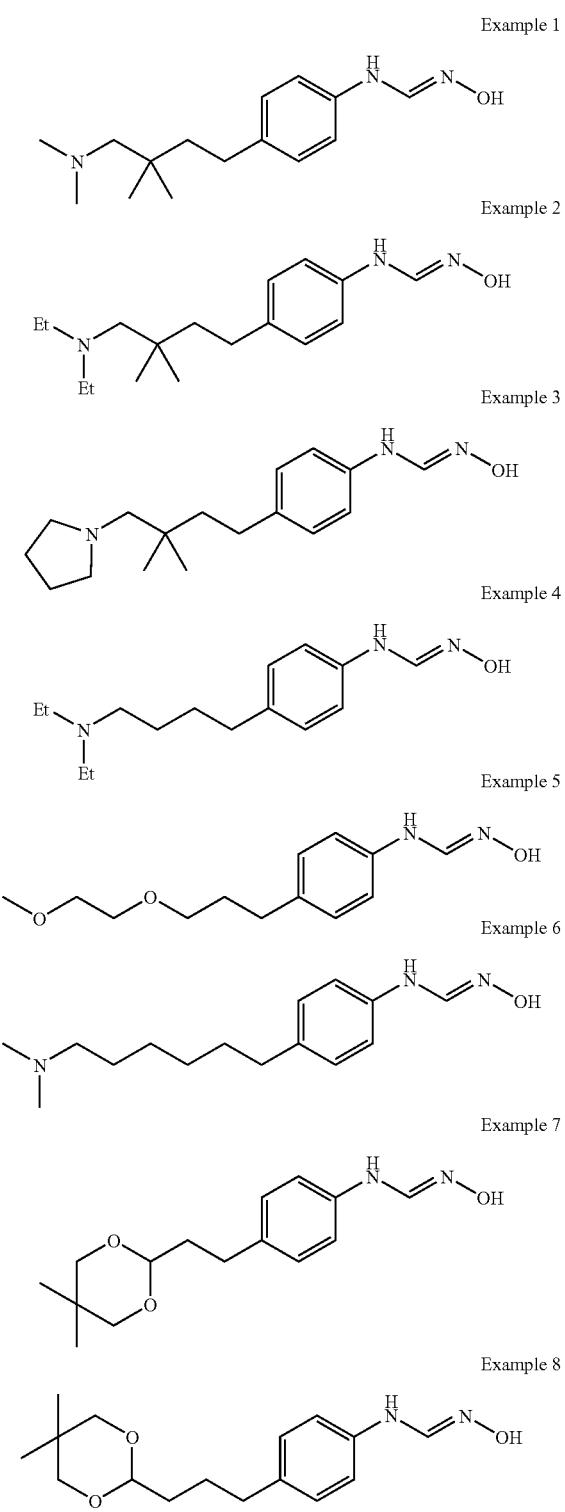

TEST EXAMPLE

Inhibitory Effect Against Human Kidney Microsome-derived 20-HETE-producing Enzyme The compounds listed in the table above were tested for their inhibitory effect against 20-HETE production.

This test was performed as described in J. Pharmacol. Exp. Ther., vol. 268, p. 474, 1994.

A test drug solution adjusted with DMSO to 1 μM was added to 50 mM 3-morpholinopropanesulfonate (MOPS) buffer (pH 7.4) containing 5 mM magnesium chloride and 1 mM ethylenediaminetetraacetic acid disodium salt (EDTA). The resulting mixture was further supplemented with a human kidney microsomal fraction (Human Cell Culture Center, Anatomic Gift Foundation) as an enzyme source, [5,6,8,9,11,12,14,15]tritium-arachidonic acid as a substrate, and NADPH as a coenzyme, followed by reaction at 37° C. for 1.5 hours. After addition of formic acid to stop the reaction, the reaction mixture was supplemented with acetonitrile (final concentration: 50%). The level of 20-HETE production was measured by high performance liquid chromatography using an ODS column (Biosil C18, BioRad Laboratories) and a radioisotope detector. Assuming that the level of 20-HETE production in the absence of a test compound was set to 100%, the concentration required for the test compound to cause 50% inhibition of 20-HETE production was calculated ($IC_{50}$ value). Table 1 shows the result obtained.

TABLE 1

| Compound | $IC_{50}$ (nM) |
| --- | --- |
| Compound of Example 1 | 10.5 |

INDUSTRIAL APPLICABILITY

The compounds according to the present invention have an inhibitory effect against 20-HETE production and are useful as therapeutic agents for 20-HETE-associated diseases in human subjects and animals, including various kidney diseases, cerebrovascular diseases and various cardiovascular diseases.

The invention claimed is:

1. An N-hydroxyformamidine compound of the following formula or a pharmaceutically acceptable salt thereof:

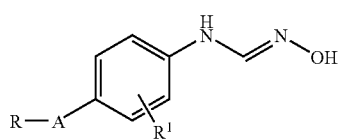

(wherein
$R^1$ represents a hydrogen atom, a $C_{1-4}$ alkyl group, a $C_{1-4}$ alkoxy group or a halogen atom, A represents a $C_{1-10}$ alkylene group or a group of the following formula:

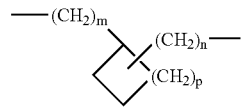

(wherein m, n and p each represent an integer of 0 to 4), and R represents an N,N-di-$C_{1-6}$ alkylamino group, a dioxanyl group, a $C_{1-4}$ alkyl-substituted dioxanyl group, a $C_{1-4}$ alkoxy-$C_{1-4}$ alkoxy group or a group of the following formula:

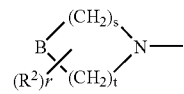

(wherein s and t each represent an integer of 1 to 4, B represents a methylene group, an oxygen atom, a sulfur atom, a nitrogen atom, a $C_{1-4}$ alkyl-substituted nitrogen atom, a phenyl-substituted nitrogen atom or a benzyl-substituted nitrogen atom, $R^2$ represents a hydrogen atom or a $C_{1-4}$ alkyl group, and r represents an integer of 0 to 2)).

2. An N-hydroxyformamidine compound of the following formula or a pharmaceutically acceptable salt thereof:

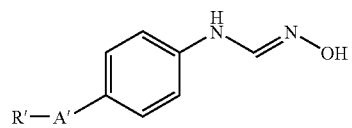

(wherein A' represents a $C_{1-10}$ alkylene group and R' represents an N,N-di-$C_{1-6}$ alkylamino group, a pyrrolidinyl group, a dioxanyl group, a CIA alkyl-substituted dioxanyl group or a $C_{1-4}$ alkoxy-$C_{1-4}$ alkoxy group).

3. A pharmaceutical preparation, which comprises the N-hydroxyformamidine compound according to claim 1 or 2 or a pharmaceutically acceptable salt thereof as an active ingredient.

4. A method of treatment for kidney disease, said method comprising administering to a subject in need thereof an effective amount of the compound according to claim 1 or 2 or a pharmaceutically acceptable salt thereof.

* * * * *